United States Patent [19]

Kuta

[11] 4,254,043
[45] Mar. 3, 1981

[54] METHOD FOR THE ACYLATION OF HETEROCYCLIC COMPOUNDS

[75] Inventor: George S. Kuta, Ft. Pierce, Fla.

[73] Assignee: American Cyanamid Company, Stamford, Conn.

[21] Appl. No.: 139,365

[22] Filed: Apr. 11, 1980

[51] Int. Cl.³ .......................................... C07D 307/46
[52] U.S. Cl. .............................. 260/347.4; 260/326.2; 260/326.37; 260/326.46; 260/326.5 J; 260/345.8 R; 260/345.9 R; 260/347.8; 546/262; 546/314; 546/328; 549/14; 549/59; 549/70; 549/72; 549/73
[58] Field of Search ........... 260/326.2, 326.37, 326.46, 260/326.5 J, 345.8 R, 345.9 R, 347.4, 347.8; 546/262, 314, 328; 549/14, 59, 70, 72, 73

[56] References Cited

U.S. PATENT DOCUMENTS

| | | | |
|---|---|---|---|
| 2,492,629 | 12/1949 | Hartough et al. | 260/347.8 X |
| 2,963,488 | 12/1960 | Webb | 260/347.8 X |

*Primary Examiner*—Richard Raymond
*Attorney, Agent, or Firm*—Richard J. Hammond

[57] ABSTRACT

A process is disclosed for the single step acylation of heterocyclic aryl compounds of the formula:

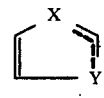

wherein X is the radical selected from the group —N=, —NH—, —O— and —S— and Y is the radical selected from the group —CH— and —CH=CH— by treatment with a compound of the formula

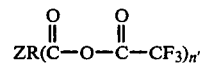

wherein R is $C_1$ to $C_{12}$ alkylene; Z is selected from the group hydrogen, cyano, halo, $C_1$ to $C_6$ alkoxy, $C_1$ to $C_6$ alkoxy carbonyl, unsubstituted or substituted phenyl, the substituents selected from the group $C_1$ to $C_6$ alkyl, $C_1$ to $C_6$ alkoxy, cyano, halo and trifluoromethyl; and n' is the integer 1 or 2.

9 Claims, No Drawings

METHOD FOR THE ACYLATION OF HETEROCYCLIC COMPOUNDS

FIELD OF INVENTION

This invention relates to a process for the preparation of alkyl heterocyclic aryl ketones by the direct acylation of a hetero aryl compound. More particularly, this invention relates to a process for the preparation of alkyl heterocyclic aryl ketones by treating a heterocyclic aryl compound with a multifunctional trifluoroacetic anhydride or bisanhydride.

FLOWSHEET A

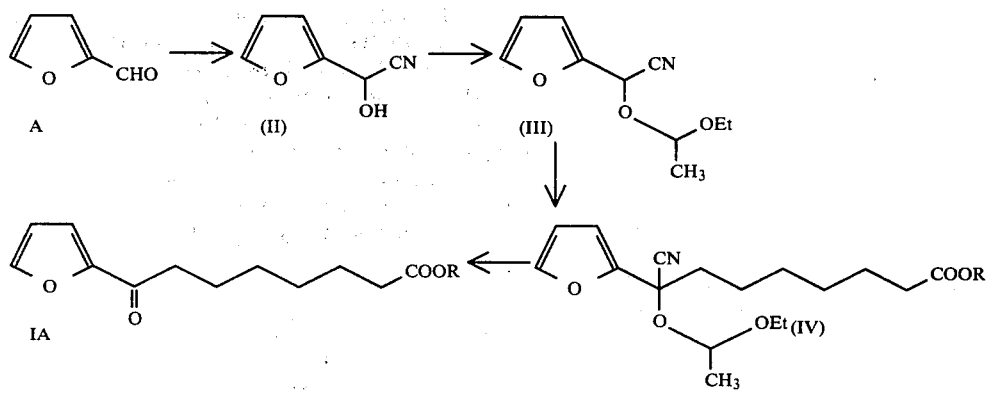

PRIOR ART

Heretofore, the preparation of heterocyclic substituted ketones has generally required a number of preparative steps with diminishing yields. For example, in accordance with the most common prior art technique as seen in Flowsheet A hereinabove, furfural cyanohydrin II is prepared from furfural A and subsequently reacted with ethyl vinyl ether in the presence of an acid catalyst, preferably dichloro-O-protected cyanohydrin forming (III) which is converted to an anionic species by treatment with a very strong base, preferably lithium diisopropylamide in an inert solvent. The resulting species is treated with a 7-haloheptanoate ester in an alkylation reaction to provide the ester cyanohydrin ether IV. The preferred alkylating agent is ethyl 7-bromoheptanoate. The preferred solvent for the conversion is tetrahydrofuran. It is advantageous to employ a higher polar complexing agent in the alkylation phase of the reaction. For this purpose a 10–20% molar excess of hexamethylphosphoric triamide (HMPA) or N-methyl-2-pyrrolidone as a mixture with the ether III may be added to a mixture of the strong base and solvent at low temperature, preferably −78° to −50°. After a suitable period, for example 30 minutes at −78°, the mixture is treated with the alkylating agent dropwise. The resulting mixture is allowed to warm to room temperature slowly over a period of several hours. The principle involved in the alkylation of cyanohydrin ethers is described in the chemical literature [J. Am. Chem. Soc., 93, 5286(1971)].

The alkylated cyanohydrin ether IV is then hydrolyzed to the parent ketone V by sequential treatment with acid and base. For example, a solution IV in tetrahydrofuran is reacted at room temperature with dilute hydrochloric acid. The crude cyanohudrin obtained as a solution by ether extraction is washed with dilute sodium hydroxide solution to afford a solution of the ketone V. The pure ketone is isolated and purified by procedures well-known in the art.

The ester group, if desired, may be saponified to afford the free carboxylic acid in the usual way, for example, with potassium hydroxide in aqueous methanol at room temperature. In this case the ketoacid (V, R=H), is In an attempt to avoid the arduous five-step route producing product IA in only 7.3% overall yield, a subsequent in yields of around 50% by a single step direct acylation procedure shown herein below in Flowsheet B.

FLOWSHEET B

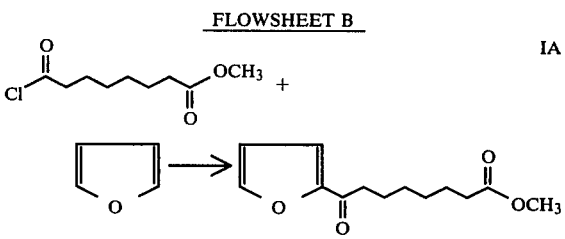

The process involved the use of equimolar amounts of methyl 7-chlorocarbonylheptanoate and anhydrous tin IV chloride in dry chloroform at −50° C. Compounds IA was obtained in about 50% yield after tedious work-up. Further, scale-up of such procedure is well recognized to present enormous engineering problems. The process of the present invention typically results in the isolation of the compounds of formula I in over 90% yield.

SUMMARY OF THE INVENTION

In summary, the present invention relates to a process for preparing compounds of the formula

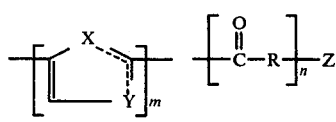

wherein X is the radical selected from the group —N=, —NH—, —O— and —S—; R is $C_1$ to $C_6$ alkylene; Z is selected from the group hydrogen, cyano, halo, $C_1$ to $C_6$ alkoxy, $C_1$ to $C_6$ alkoxycarbonyl, unsubstituted or substituted phenyl, the substituents selected from the group $C_1$ to $C_6$ alkyl, $C_1$ to $C_6$ alkoxy, cyano, halo and trifluoromethyl; Y is the radical selected from the group —CH— and —CH=CH—; m and n are identical or different and are whole integers having a value of at least one; and where X is the radical —N= or —NH—, the pharmaceutically acceptable, non-toxic salts thereof which comprises treating a compound of the formula

where X and Y are as previously defined, with a compound of the formula

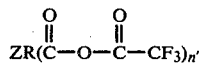

wherein R and Z are as previously defined and n' is the integer 1 or 2 and separating the compound of formula I. The process is carried out in the presence of an inert organic, polar solvent at temperatures of from about 0° to 75° resulting in substantially greater yields of the compounds of formula I than any of the prior art processes.

DESCRIPTION OF THE PREFERRED EMBODIMENTS

Included in the compounds generically represented by those of formula I are the following subgenera IA through IC:

(1.) 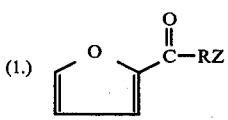 IA wherein R and Z are as previously defined.

In the compounds of formula IA, it is preferred that R is $C_1$ to $C_9$ alkylene and Z is selected from the group hydrogen, cyano, bromo, chloro, carbomethoxy, carboethoxy and phenyl. Most preferred are those compounds of formula IA where R is —$CH_2$— and Z is cyano; R is —$(CH_2)_6$— and Z is carboethoxy; R is —$(CH_2)_6$— and Z is carbomethoxy; R is —$(CH_2)_5$— or —$(CH_2)_6$— and Z is bromo; and R is —$(CH_2)_4$—, —$(CH_2)_5$—, —$(CH_2)_6$—, —$(CH_2)_7$—, —$(CH_2)_8$—, or —$(CH_2)_9$— and Z is hydrogen.

(2.) 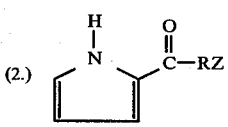 IB wherein R and Z are as previously defined.

In the compounds of formula IB, it is preferred that R is $C_1$ to $C_9$ alkylene and Z is selected from the group hydrogen, cyano, bromo, chloro, carbomethoxy, carboethoxy and phenyl. Most preferred are those compounds of formula IB where R is —$CH_2$— and Z is cyano; R is —$(CH_2)_6$— and Z is carboethoxy; R is —$(CH_2)_6$— and Z is carbomethoxy; R is —$(CH_2)_5$— or —$(CH_2)_6$— and Z is bromo; and R is —$(CH_2)_4$—, —$(CH_2)_5$—, —$(CH_2)_6$—, —$(CH_2)_7$—, —$(CH_2)_8$—, or —$(CH_2)_9$— and Z is hydrogen.

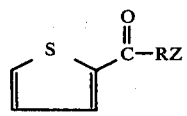 IC wherein R and Z are as previously defined.

In the compounds of formula IC, it is preferred that R is $C_1$ to $C_9$ alkylene and Z is selected from the group hydrogen, cyano, bromo, chloro, carbomethoxy, carboethoxy and phenyl. Most preferred are those compounds of formula IC where R is —$CH_2$— and Z is cyano; R is —$(CH_2)_6$— and Z is carboethoxy; R is —$(CH_2)_5$— N and Z is carbomethoxy, R is —$(CH_2)_5$— or —$(CH_2)_6$— and Z is bromo; and R is —$(CH_2)_4$—, —$(CH_2)_5$—, —$(CH_2)_6$—, —$(CH_2)_7$, —$(CH_2)_8$— or —$(CH_2)_9$— and Z is hydrogen.

The novel process of this invention useful for the preparation of the compounds of formula I comprises the treatment of a heterocyclic aryl compound of the formula:

wherein X is the radical selected from the group —N=, —NH—, —O— and —S— and Y is the radical selected from the group —CH— and —CH=CH—, with a compound of the formula

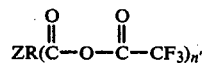

wherein R is $C_1$ to $C_{12}$ alkylene; Z is selected from the group hydrogen, cyano, halo, $C_1$ to $C_6$ alkoxy, $C_1$ to $C_6$ alkoxycarbonyl, unsubstituted or substituted phenyl, the substituents selected from the group $C_1$ to $C_6$ alkyl, $C_1$ to $C_6$ alkoxy, cyano, halo and trifluoromethyl; and n' is the integer 1 or 2. Typically, equimolar amounts of the heterocyclic aryl compound and the ZR-substituted trifluoroacetic anhydride dissolved or dispersed in an inert organic solvent are allowed to react over a period of 30 minutes to 48 hours at about 0° to 75°. Under the conditions described heretofore the products formed are substantially those illustrated by the subgeneric structures IA to IC. However, by changing the stoichiometry of the reacting compounds or by varying the temperature, time or solvent used in the reaction, varying products can be obtained all having the generic formula I. Thus, the use of two equivalents of the heterocyclic aryl compound for each equivalent of anhydride, where n' is the integer 2, gives rise to compounds of formula II.

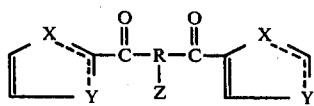 II

Conversely, by the treating of one equivalent of the heterocyclic aryl compound with two equivalents of anhydride, (n'=1), the compounds of formula III are formed.

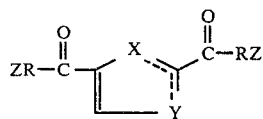

In those cases where the anhydride is difunctional, i.e., where n' is the integer 2, the use of equivalent amounts of such anhydride with the heterocyclic aryl compound produces high molecular weight polymers of the formula:

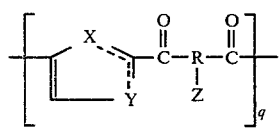

where X, Y, R and Z are as previously defined and q is an integer of from about 10 to about 20,000.

The R-substituted trifluoroacetic anhydride (or bisanhydride when n'=2) is typically prepared by treating equivalent amounts of trifluoroacetic anhydride with a suitable aliphatic carboxylic acid (or dibasic acid for those cases where n'=2), i.e.,

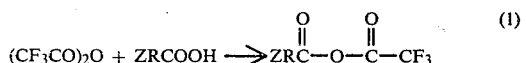

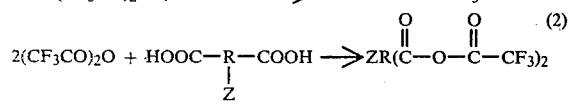

The R-substituted anhydride forms readily at reaction temperatures of from about 0° to about 75°, preferably about 25° in times of 15 minutes to 48 hours. Polar, inert organic solvents are preferably used in this reaction such illustrated by methylene chloride, chloroform, trichloroethylene, dimethylformamide, etc. Separation and isolation of the R-substituted trifluoroacetic anhydride can be effected by any suitable purification procedure such as, for example, evaporation, crystallization, column chromatography, thin-layer chromatography, distillation, etc. Specific illustrations of typical separation and isolation procedures can be had by reference to the appropriate examples described hereinbelow; however, other equivalent separation procedures can, of course, also be used. Preferably, the anhydride is employed directly, without further isolation from the reaction (1) or (2). It should be appreciated that where typical reaction conditions (e.g., temperatures, mole ratios, reactions times) have been given, that conditions both somewhat above and below these ranges can also be used, though generally less conveniently. The process of the present invention provides high yields of compounds of formula I (typically greater than 70% and, in the majority of reactions 90% or greater) in what is essentially a single step reaction.

Illustrative of how the compounds prepared by the novel process disclosed and claimed herein can be used, the ketone IA prepared by the process of the present invention is converted to the furylcarbinol VIII (Flowsheet C) by a reduction process. The most-favored method utilizes a mixture of sodium borohydride and ethanol at a temperature of 20°-35° C. for several hours. The ester of acid IA is isolated by any suitable well-known procedure.

The conversion of the α-(6-carboxyhexyl)furfuryl alcohol derivatives (VIII) to the useful intermediate XI is further outlined in Flowsheet C. According to the pathway shown therein, the furylcarbinol VII is treated with an acid catalyst in a mixed aqueous-organic solvent. Representative acid catalysts are formic acid, trichloroacetic acid, dichloroacetic acid, phosphoric acid, and p-toluenesulfonic acid. Inert, non-hydroxylic, water-miscible organic solvents such as acetone, dioxane, dimethoxyethane, tetrahydrofuran, and dimethylsulfoxide are used in a suitable proportion with water as solvent for the reaction. A preferred system is 3:2 (V/V)dioxane-water. The optimal temperature for the reaction is in the range 50°-100° C.

Acids stronger than the aforementioned catalysts are not as suitable since they augment the formation of by-products.

The product of the first stage of the reaction is the linear enedione(IX) [U.S. Pat. No. 3,952,033]. On occasion this intermediate may be isolated. However, the preferred procedure entails maintenance of the reaction conditions until formation of cyclopentenone (X) is complete.

The substance (X) may be isolated at this stage or used in situ for the next step. In the latter case a strong acid such as sulfuric acid or perchloric acid is added to the solution, and the reaction is run until the equilibrium mixture of (X) and (XI) is obtained. This results in formation of more than 90% (XI) from (X). A preferred set of conditions is 2 N sulfuric acid in the above solvent, a temperature of 60°, and a reaction time of 20 hours. Under these conditions, the ester group of (X), if present, is hydrolyzed to a carboxyl group. The product (XI) is isolated by well-known procedures.

If the intermediate cyclopentenone (X) is isolated, the subsequent isomerization to (XI) may be accomplished by a variety of means. The compound (X) may be treated with a solution of strong acid such as sulfuric acid or perchloric acid in a mixture of water and an inert, water-miscible, nonhydroxylic organic solvent. The isomerization may also be effected with an aqueous solution of a weak base such as sodium carbonate. Another procedure employs a solution of triethylamine and chloral in an inert solvent such as dichloromethane [J. Am. Chem. Soc., 97, 3258(1975)]. In each case the product (XI) is isolated by well-known procedures.

FLOWSHEET C

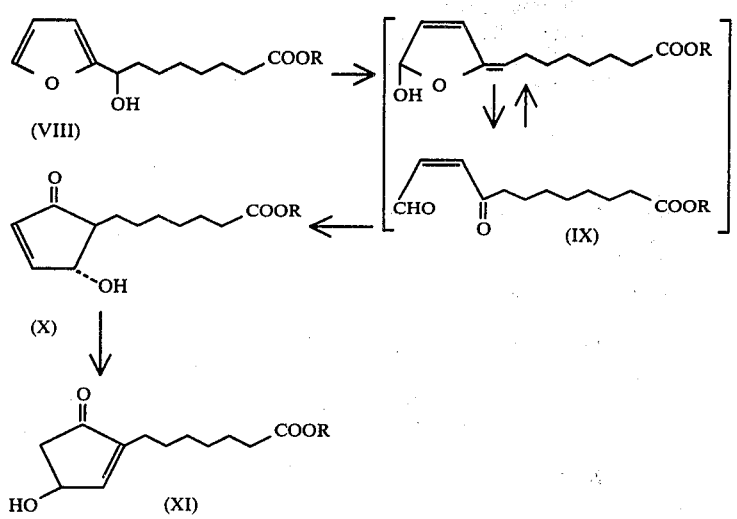

The conversion of cyclopentenone (XI) to prostaglandins is a well-known general method. For the preparation of d,l-prostaglandin E, (d,l-PGE$_1$) (XIII), the cyclopentenone (XI) (R=H) is converted to, for example, a bis-tetrahydropyranyl or a bis-trimethylsilyl derivative (XIII) by commonly used methods. The resulting protected compound is converted to (XIII) by conjugate addition of a suitable vinyl metal species [see, for example, PROSTAGLANDINS, 3,921 (1973) and Flowsheet D].

For the preparation of l-PGE$_1$, methyl ester (XV), the cyclopentenone (XI) (R=CH$_3$) is subjected to chemical resolution to afford the (4R) enantiomer [see Tetrahedron Letters, 1973, 943]. The tetrahydropyranyl ether (XIV) has been converted to (XV) [J. Am. Chem. Soc., 97, 865 (1975)]; see Flowsheet D.

The above procedures are described with some particularity in U.S. Pat. No. 4,026,732 incorporated herein by reference.

The following terms as used hereinabove and below, have the following meaning unless expressly stated to the contrary. The term "C$_1$ to C$_{12}$ alkylene" refers to a saturated, unbranched, or branched acyclic divalent hydrocarbon group containing 1 to 12 carbon atoms, such as methylene, ethylene, propylene, and the like. When employing the term "substituted phenyl" what is meant is the aromatic phenyl group having mono or di-substituents selected from the group C$_1$ to C$_6$ alkyl, C$_1$ to C$_6$ alkoxy, cyano, halo and trifluoromethyl, "alkyl" in this case referring to the monovalent species of linear or branched C$_1$ to C$_6$ acyclic hydrocarbon radicals. The term "halo" or "halide" refers to fluoro, chloro, bromo or iodo or the corresponding halides. The term "pharmaceutically acceptable salts" refers to

FLOWSHEET D

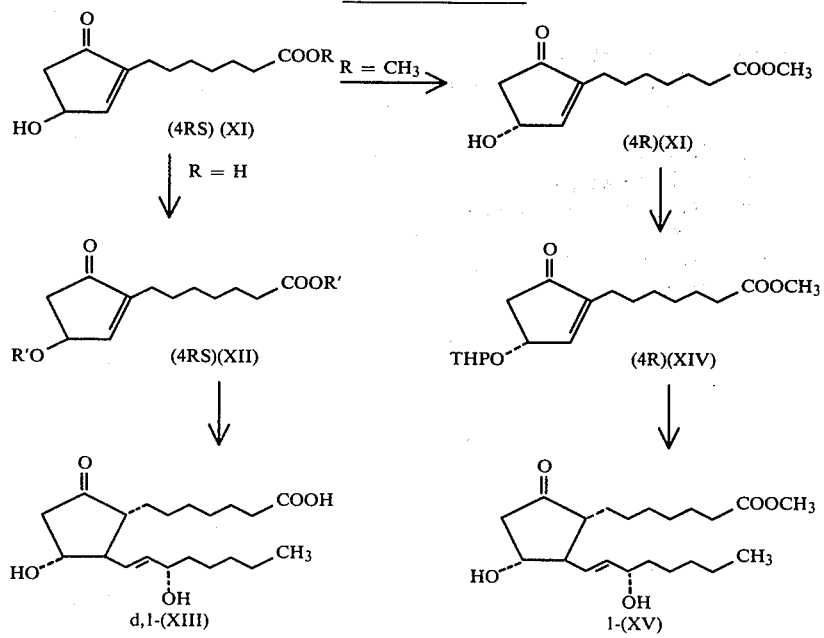

those salts of the parent compound which do not adversely effect the pharmaceutical properties (e.g., toxicity, effectiveness, etc.) of the parent compound, such as, for example, are conventionally used in the pharmaceutical art. The salts of the present invention are pharmaceutically acceptable anion salts, with respect to the X moiety when such is —N= or —NH—. Suitable pharmaceutically acceptable anions include, for example, the halides, sulfate, carboxylate, etc.

In the following examples and elsewhere in the specification, all temperatures are in degrees centigrade. Room temperature refers to about 23°.

EXAMPLE 1

In a typical reaction for the preparation of the compounds of formulae IA-C 130 mmol of an aliphatic carboxylic acid is dissolved in 200 ml of dry methylene chloride and placed in a round-bottomed flask equipped with a stir bar and an addition funnel.

Trifluoroacetic anhydride (135 mmol) is dissolved in 50 ml of dry methylene chloride and added in a steady stream to the stirred aliphatic acid solution.

After 15 minutes, 390 mmol of the heterocyclic aryl compound in 25 ml. of dry methylene chloride is added in a steady stream to the mixed anhydride solution, then stirred at room temperature for two hours.

The solvent and trifluoroacetic acid are stripped in vacuo. The residue is taken up in ether, washed with water, dried, then distilled under vacuum.

In this manner, employing furan as the heterocyclicaryl compound and the appropriate ZR-substituted aliphatic carboxylic acid, the following compounds are prepared:

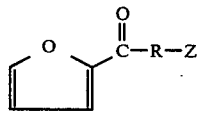

| R | Z | % yield | B.P. |
|---|---|---|---|
| —(CH$_2$)$_6$— | $-\overset{\overset{O}{\|}}{C}-OC_2H_5$ | 92.6 | 137–143° (0.001mm) |
| —(CH$_2$)$_6$— | $-\overset{\overset{O}{\|}}{C}-OC$ | 92 | 136–137° (0.001mm) |
| —(CH$_2$)$_5$— | Br | 93 | 108–110° (0.01mm) |
| —(CH$_2$)$_6$— | Br | 90 | 114° (0.001mm) |
| —CH$_2$— | CN | 75 | mp 75° |
| —(CH$_2$)$_4$— | H | 92 | 48–50° C. (0.01mm) |
| —(CH$_2$)$_5$— | H | 93 | 64–66° C. (0.075mm) |
| —(CH$_2$)$_6$— | H | 91 | 78–79° C. (0.03mm) |
| —(CH$_2$)$_7$— | H | 93 | 87–89° C. (0.01mm) |
| —(CH$_2$)$_8$— | H | 91 | 68–69° (0.025m) |
| —(CH$_2$)$_9$— | H | 91 | 90–91° (0.175mm) |

EXAMPLE 2

In a typical reaction for the preparation of the compounds of formula II, 130 mmol of a debasic aliphatic carboxylic acid is dissolved in 200 ml. of dry methylene chloride and placed in a round-bottom flask equipped with a stir bar and an addition funnel.

Trifluoroacetic anhydride (135 mmol) is dissolved in 50 ml. of dry methylene chloride and added in a steady stream to the stirred aliphatic acid solution. After 15 minutes, 780 mmol of the heterocyclic aryl compound in 50 ml of dry methylene chloride is added in a steady stream to the mixed anhydride solution, then stirred at room temperature for two hours. The solvent and trifluoroacetic acid are removed in vacuo. The residue is taken up in ether, washed with water, dried and vacuum distilled.

In this manner the following compounds are prepared (heterocyclic aryl compound, dibasic carboxylic acid):

difur-2-ylhexan-1,6-dione (furan, adipic acid);
dithien-2-ylhexan-1,6-dione (thiophene, adipic acid); and
dipyrol-2-ylhexan-1,6-dione (ptrrole, adipic acid).

EXAMPLE 3

In a typical reaction for the preparation of the compounds of formula III, 260 mmol of an aliphatic carboxylic acid is dissolved in 200 ml. of dry methylene chloride and placed in a round-bottomed flask equipped with a stir bar and an addition funnel.

Trifluoroacetic anhydride (270 mmol) is dissolved in 50 ml. of dry methylene chloride and added in a steady stream to the stirred aliphatic acid solution.

After 15 minutes, 390 mmol of the heterocyclic aryl compound in 25 ml. of dry methylene chloride is added in a steady stream to the mixed anhydride solution, then stirred at room temperature for two hours.

The solvent and trifluoroacetic acid are stripped in vacuo. The residue is taken up in ether, washed with water, dried, then distilled under vacuum.

In this manner, the following compounds are prepared (heterocyclic aryl compound, aliphatic carboxylic acid):

di(1-oxopropyl)-2,4-furan (furan, n-butyric acid);
di(1-oxo-3-cyanohexyl)-2,4-furan(furan,3-cyanohexanoic acid);
di(1-oxo-3-bromohexyl)-2,4-furan(furan,3-bromohexanoic acid); and
di(1-oxo-6-chlorohexyl)-2,4-furan(furan,6-chlorohexanoic acid).

EXAMPLE 4

In a typical reaction for the preparation of the macromolecules of formula IV 130 mmol of an aliphatic dibasic acid is dissolved in 200 ml. of dry methylene chloride and placed in a round-bottomed flask equipped with a stir bar and an addition funnel.

Trifluoroacetic anhydride (270 mmol) is dissolved in 50 ml. of dry methylene chloride and added in a steady stream to the stirred aliphatic acid solution.

After 15 minutes 390 mmol of the heterocyclic aryl compound in 25 ml. of dry methylene chloride is added in a steady stream to the mixed anhydride solution, then stirred at room temperature for two hours.

The solvent and trifluoroacetic acid are stripped in vacuo. The residue is taken up in ether, washed with water, dried, then distilled under vacuum.

In this manner, employing furan as the heterocyclic aryl compound the following macromolecules are prepared (dibasic carboxylic acid):

poly(ketotetramethylene-2,4-furan), (adipic acid); and
poly(ketohexamethylene-2,4-furan), (suberic acid).

It will be apparent that many widely different embodiments of this invention may be made without departing from the spirit and scope thereof and, therefore, it is not intended to be limited in any way except as indicated in the appended claims.

I claim:

1. A process for preparing the compound of the formula:

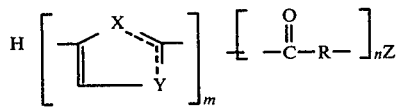   I wherein X is the radical selected from the group —N=, —NH—, —O— and —S—; R is $C_1$ to $C_{12}$ alkylene; Z is selected from the group hydrogen, cyano, halo, $C_1$ to $C_6$ alkoxy, $C_1$ to $C_6$ alkoxycarbonyl, and unsubstituted or substituted phenyl, the substituents selected from the group $C_1$ to $C_6$ alkyl, $C_1$ to $C_6$ alkoxy, cyano, halo and trifluoromethyl; Y is the radical selected from the group —CH— and —CH=CH—; m and n are identical or different and are whole integers having a value of at least 1; and, where X is the radical —N= or —NH—, the pharmaceutically acceptable non-toxic salts thereof which comprises treating a compound of the formula

where X and Y are as previously defined with a compound of the formula

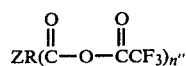

wherein R and Z are as previously defined and n' is the integer 1 or 2 and separating the compound of formula I.

2. The process according to claim 1 wherein X is the radical —O—, Y is the radical —CH—, and R, Z, m and n are as previously defined.

3. The process according to claim 2 wherein m and n are identical and are the integer 1, and R and Z are as previously defined.

4. The process according to claim 3 wherein R is $C_1$ to $C_9$ alkylene and Z is selected from the group hydrogen, cyano, bromo, chloro, carbomethoxy, carboethoxy and phenyl.

5. The process according to claim 4 wherein R is —$CH_2$— and Z is cyano.

6. The process according to claim 4 wherein R is —$(CH_2)_6$— and Z is carboethoxy.

7. The process according to claim 4 wherein R is —$(CH_2)_6$ and Z is carbomethoxy.

8. The process according to claim 4 wherein R is —$(CH_2)_5$ or —$(CH_2)_6$— and Z is bromo.

9. The process according to claim 4 wherein R is —$(CH_2)_4$—, —$(CH_2)_5$—, —$(CH_2)_6$—, —$(CH_2)_7$, —$(CH_2)_8$— or $(CH_2)_9$ and Z is hydrogen.

* * * * *